US012751833B2

(12) United States Patent
Helmar

(10) Patent No.: US 12,751,833 B2
(45) Date of Patent: Oct. 6, 2026

(54) SENSOR ENABLED INTERBODY IMPLANTS AND METHODS FOR MANUFACTURING SAME

(71) Applicant: NANOHIVE MEDICAL LLC, Woburn, MA (US)

(72) Inventor: Ian Helmar, Beverly, MA (US)

(73) Assignee: NANOHIVE MEDICAL INC., Woburn, MA (US)

( * ) Notice: Subject to any disclaimer, the term of this patent is extended or adjusted under 35 U.S.C. 154(b) by 0 days.

(21) Appl. No.: 19/565,296

(22) Filed: Mar. 12, 2026

(65) Prior Publication Data

US 2026/0272667 A1 Sep. 17, 2026

Related U.S. Application Data

(60) Provisional application No. 63/770,387, filed on Mar. 12, 2025.

(51) Int. Cl.

*A61F 2/44* (2006.01)
*A61F 2/30* (2006.01)
*A61F 2/46* (2006.01)

(52) U.S. Cl.

CPC .......... *A61F 2/442* (2013.01); *A61F 2/30734* (2013.01); *A61F 2/3094* (2013.01); *A61F 2/4455* (2013.01); *A61F 2002/30593* (2013.01); *A61F 2002/3067* (2013.01); *A61F 2002/3092* (2013.01); *A61F 2002/4666* (2013.01)

(58) Field of Classification Search

CPC ........................................................ A61F 2/442
See application file for complete search history.

(56) References Cited

U.S. PATENT DOCUMENTS 5,059,193 A 10/1991 Kuslich
5,615,528 A 4/1997 Owens
5,674,294 A 10/1997 Bainville et al.
6,042,582 A * 3/2000 Ray .................... A61B 17/1757 606/247
6,099,531 A * 8/2000 Bonutti ............... A61F 2/30734 606/88
6,149,688 A 11/2000 Brosnahan et al.
6,159,244 A 12/2000 Suddaby et al.
(Continued)

FOREIGN PATENT DOCUMENTS

CA 3106538 1/2020
CN 204971711 1/2016
(Continued)

OTHER PUBLICATIONS

Ahmadi, S. et al., "Additively Manufactured Open-Cell Porous Biomaterials Made from Six Different Space-Filling Unit Cells: The Mechanical and Morphological Properties," Materials, vol. 8:1871-1896 (2015).

(Continued)

*Primary Examiner* — Christian A Sevilla
(74) *Attorney, Agent, or Firm* — McDermott Will & Schulte LLP

(57) ABSTRACT

A sensor-enabled implant is disclosed. The sensor-enabled implant includes two endplates that are separated via a low stiffness body. A sensor is disposed within an implant body along a loading direction of the implant such that it measures a load applied to a loadbearing endplate of the implant.

13 Claims, 8 Drawing Sheets

(56) References Cited

U.S. PATENT DOCUMENTS

| | | | | |
|---|---|---|---|---|
| 6,176,882 | B1 * | 1/2001 | Biedermann | A61F 2/447 623/17.11 |
| 6,193,757 | B1 | 2/2001 | Foley | |
| 6,206,924 | B1 | 3/2001 | Timm | |
| 6,723,126 | B1 | 4/2004 | Berry | |
| 6,767,594 | B1 | 7/2004 | Miroshin | |
| 6,902,579 | B2 | 6/2005 | Harms et al. | |
| 6,984,234 | B2 | 1/2006 | Bray | |
| 6,993,406 | B1 | 1/2006 | Cesarano, III et al. | |
| 7,128,760 | B2 | 10/2006 | Michelson | |
| 7,172,627 | B2 | 2/2007 | Fiere | |
| 7,217,293 | B2 | 5/2007 | Branch, Jr. | |
| 7,232,594 | B2 | 6/2007 | Miroshin et al. | |
| 7,637,950 | B2 | 12/2009 | Baccelli et al. | |
| D619,255 | S | 7/2010 | Richter et al. | |
| 7,799,079 | B2 | 9/2010 | Hestad et al. | |
| D626,233 | S | 10/2010 | Cipoletti et al. | |
| 7,846,207 | B2 | 12/2010 | Lechmann et al. | |
| 7,850,731 | B2 | 12/2010 | Brittan et al. | |
| 8,043,381 | B2 | 10/2011 | Hestad et al. | |
| D653,757 | S | 2/2012 | Binder | |
| 8,236,058 | B2 | 8/2012 | Fabian et al. | |
| 8,425,576 | B2 | 4/2013 | Anderson | |
| D682,427 | S | 5/2013 | Farris et al. | |
| D692,136 | S | 10/2013 | Tyber | |
| 8,663,332 | B1 | 3/2014 | To | |
| 8,697,231 | B2 | 4/2014 | Longepied et al. | |
| 8,740,983 | B1 | 6/2014 | Arnold et al. | |
| D708,747 | S | 7/2014 | Curran et al. | |
| D711,537 | S | 8/2014 | Pimenta et al. | |
| 8,900,307 | B2 | 12/2014 | Hawkins et al. | |
| 8,945,227 | B2 | 2/2015 | Kirschman | |
| 9,005,291 | B2 | 4/2015 | Loebl et al. | |
| D737,446 | S | 8/2015 | Butler et al. | |
| 9,155,819 | B2 | 10/2015 | Fonte et al. | |
| 9,186,257 | B2 | 11/2015 | Geisler | |
| D750,249 | S | 2/2016 | Grimberg, Jr. et al. | |
| 9,271,836 | B2 | 3/2016 | Pavento | |
| 9,271,843 | B2 | 3/2016 | Fabian et al. | |
| 9,271,845 | B2 | 3/2016 | Hunt | |
| 9,308,076 | B2 | 4/2016 | Ringeisen et al. | |
| 9,421,108 | B2 | 8/2016 | Hunt | |
| 9,427,330 | B2 | 8/2016 | Petersheim et al. | |
| 9,456,901 | B2 | 10/2016 | Jones et al. | |
| 9,492,285 | B2 | 11/2016 | Saidha et al. | |
| 9,566,163 | B2 | 2/2017 | Suddaby et al. | |
| 9,649,200 | B2 | 5/2017 | Wickham | |
| 9,662,225 | B2 | 5/2017 | Pavento | |
| 9,662,226 | B2 | 5/2017 | Wickham | |
| D789,539 | S | 6/2017 | Kleiner et al. | |
| 9,668,877 | B2 | 6/2017 | Pavento | |
| 9,713,537 | B2 | 7/2017 | Bray | |
| 9,782,270 | B2 | 10/2017 | Wickham | |
| 9,872,781 | B2 | 1/2018 | Pavento | |
| D816,844 | S | 5/2018 | Ricca et al. | |
| 9,962,269 | B2 | 5/2018 | Jones et al. | |
| 10,045,797 | B1 | 8/2018 | Walkenhorst | |
| 10,052,212 | B2 | 8/2018 | Flechter et al. | |
| D833,012 | S | 11/2018 | Jones et al. | |
| D833,611 | S | 11/2018 | Jones et al. | |
| D833,612 | S | 11/2018 | Jones et al. | |
| 10,130,488 | B2 | 11/2018 | Saidha et al. | |
| D835,279 | S | 12/2018 | Jones et al. | |
| D835,788 | S | 12/2018 | Jones et al. | |
| D840,036 | S | 2/2019 | Jones et al. | |
| 10,368,997 | B2 | 8/2019 | Jones et al. | |
| 10,405,983 | B2 | 9/2019 | Jones et al. | |
| 10,507,118 | B2 | 12/2019 | Afzal | |
| 10,588,749 | B2 | 3/2020 | Sharp et al. | |
| 10,624,746 | B2 | 4/2020 | Jones et al. | |
| 10,675,158 | B2 | 6/2020 | Unger et al. | |
| 10,695,184 | B2 | 6/2020 | Jones et al. | |
| 10,716,673 | B2 | 7/2020 | Jones et al. | |
| 10,744,001 | B2 | 8/2020 | Sack | |
| 10,842,634 | B2 | 11/2020 | Pasini et al. | |
| 10,884,429 | B2 | 1/2021 | Jones et al. | |
| 11,026,802 | B2 | 6/2021 | Bray | |
| 11,174,911 | B2 | 11/2021 | Kang | |
| 11,278,421 | B2 | 3/2022 | Hunt | |
| 11,369,419 | B2 | 6/2022 | Mesiwala et al. | |
| 11,452,611 | B2 | 9/2022 | McShane et al. | |
| 2002/0099376 | A1 | 7/2002 | Michelson | |
| 2002/0128713 | A1 * | 9/2002 | Ferree | A61F 2/4465 623/17.11 |
| 2002/0161444 | A1 | 10/2002 | Choi | |
| 2003/0114936 | A1 | 6/2003 | Sherwood et al. | |
| 2003/0120348 | A1 | 6/2003 | Brosnahan | |
| 2004/0162618 | A1 | 8/2004 | Mujwid | |
| 2004/0243241 | A1 | 12/2004 | Istephanous | |
| 2004/0258732 | A1 | 12/2004 | Shikinami | |
| 2005/0049706 | A1 | 3/2005 | Brodke et al. | |
| 2005/0059972 | A1 | 3/2005 | Biscup | |
| 2005/0101960 | A1 | 5/2005 | Fiere | |
| 2005/0113916 | A1 | 5/2005 | Branch | |
| 2005/0129726 | A1 | 6/2005 | Liebschner | |
| 2005/0159813 | A1 | 7/2005 | Molz | |
| 2005/0251083 | A1 | 11/2005 | Carr-Brendel et al. | |
| 2006/0147332 | A1 | 7/2006 | Jones et al. | |
| 2006/0257817 | A1 | 11/2006 | Shelton | |
| 2006/0259144 | A1 | 11/2006 | Trieu | |
| 2006/0276925 | A1 | 12/2006 | Lin et al. | |
| 2007/0073398 | A1 | 3/2007 | Fabian et al. | |
| 2007/0123987 | A1 | 5/2007 | Bernstein | |
| 2007/0142914 | A1 | 6/2007 | Jones et al. | |
| 2007/0150068 | A1 | 6/2007 | Dong | |
| 2007/0233247 | A1 | 10/2007 | Schwab | |
| 2007/0270858 | A1 | 11/2007 | Trieu | |
| 2008/0161925 | A1 | 7/2008 | Brittan | |
| 2008/0161927 | A1 | 7/2008 | Savage et al. | |
| 2008/0169585 | A1 | 7/2008 | Zinniel | |
| 2008/0269903 | A1 | 10/2008 | Francis et al. | |
| 2008/0294262 | A1 | 11/2008 | Levieux | |
| 2008/0300634 | A1 | 12/2008 | Gray | |
| 2008/0306596 | A1 | 12/2008 | Jones et al. | |
| 2008/0306609 | A1 | 12/2008 | Lee et al. | |
| 2009/0012529 | A1 | 1/2009 | Blain | |
| 2009/0037148 | A1 | 2/2009 | Lin et al. | |
| 2009/0105831 | A1 | 4/2009 | Jones | |
| 2009/0182429 | A1 | 7/2009 | Humphreys et al. | |
| 2009/0287214 | A1 | 11/2009 | Yu | |
| 2009/0317278 | A1 | 12/2009 | Kokubo | |
| 2009/0326580 | A1 | 12/2009 | Anderson | |
| 2010/0010638 | A1 | 1/2010 | Jones et al. | |
| 2010/0087925 | A1 | 4/2010 | Kostuik et al. | |
| 2010/0100185 | A1 | 4/2010 | Trieu et al. | |
| 2010/0145459 | A1 | 6/2010 | McDonough et al. | |
| 2010/0234948 | A1 | 9/2010 | Khoury et al. | |
| 2010/0286783 | A1 | 11/2010 | Lechmann et al. | |
| 2011/0004307 | A1 | 1/2011 | Ahn et al. | |
| 2011/0012280 | A1 | 1/2011 | Deslauriers et al. | |
| 2011/0029084 | A1 | 2/2011 | Milbocker et al. | |
| 2011/0029087 | A1 | 2/2011 | Haider et al. | |
| 2011/0144764 | A1 | 6/2011 | Bagga et al. | |
| 2011/0190892 | A1 | 8/2011 | Kirschman | |
| 2011/0202136 | A1 | 8/2011 | Brittan et al. | |
| 2011/0224796 | A1 | 9/2011 | Weiland | |
| 2011/0282392 | A1 | 11/2011 | Murphy et al. | |
| 2012/0022653 | A1 | 1/2012 | Kirschman | |
| 2012/0123546 | A1 | 5/2012 | Medina | |
| 2012/0150299 | A1 | 6/2012 | Ergun et al. | |
| 2012/0177939 | A1 | 7/2012 | Longepied et al. | |
| 2012/0179258 | A1 | 7/2012 | Glazer et al. | |
| 2012/0185047 | A1 | 7/2012 | Wooley | |
| 2012/0215310 | A1 | 8/2012 | Sharp et al. | |
| 2012/0215313 | A1 | 8/2012 | Saidha et al. | |
| 2012/0303128 | A1 | 11/2012 | Ullrich, Jr. et al. | |
| 2012/0312779 | A1 | 12/2012 | Patterson | |
| 2012/0321878 | A1 | 12/2012 | Landon et al. | |
| 2013/0026492 | A1 | 1/2013 | Khan | |
| 2013/0039094 | A1 | 2/2013 | Kolb | |
| 2013/0060337 | A1 | 3/2013 | Petersheim | |
| 2013/0073044 | A1 | 3/2013 | Gamache | |
| 2013/0211533 | A1 | 8/2013 | Fonte et al. | |
| 2013/0218276 | A1 | 8/2013 | Fiechter et al. | |

(56) References Cited

U.S. PATENT DOCUMENTS

| | | | | |
|---|---|---|---|---|
| 2013/0238095 | A1 | 9/2013 | Pavento | |
| 2013/0282126 | A1 | 10/2013 | Saidha et al. | |
| 2013/0310939 | A1 | 11/2013 | Fabian et al. | |
| 2013/0325129 | A1 | 12/2013 | Huang | |
| 2014/0012382 | A1 | 1/2014 | Doty | |
| 2014/0012384 | A1 | 1/2014 | Kana | |
| 2014/0037873 | A1 | 2/2014 | Cheung | |
| 2014/0046447 | A1 | 2/2014 | Dunworth | |
| 2014/0046448 | A1 | 2/2014 | Kana | |
| 2014/0107786 | A1 | 4/2014 | Geisler et al. | |
| 2014/0121776 | A1 | 5/2014 | Hunt | |
| 2014/0277482 | A1 | 9/2014 | Gfeller et al. | |
| 2015/0005885 | A1 | 1/2015 | Zhang et al. | |
| 2015/0025635 | A1 | 1/2015 | Laubert | |
| 2015/0093283 | A1 | 4/2015 | Miller | |
| 2015/0100126 | A1 | 4/2015 | Melkent et al. | |
| 2015/0360421 | A1 | 12/2015 | Burhop et al. | |
| 2016/0000574 | A9 | 1/2016 | Fabian et al. | |
| 2016/0022431 | A1 | 1/2016 | Wickham | |
| 2016/0027425 | A1 | 1/2016 | Cook et al. | |
| 2016/0038301 | A1 | 2/2016 | Wickham | |
| 2016/0058480 | A1 | 3/2016 | Laubert | |
| 2016/0085882 | A1 | 3/2016 | Li et al. | |
| 2016/0113775 | A1 | 4/2016 | Willis et al. | |
| 2016/0166284 | A1 | 6/2016 | Hacking et al. | |
| 2016/0184103 | A1 | 6/2016 | Fonte et al. | |
| 2016/0199193 | A1 | 7/2016 | Willis et al. | |
| 2016/0206440 | A1 | 7/2016 | DeRidder | |
| 2016/0235546 | A1 | 8/2016 | Cheng | |
| 2016/0270931 | A1 | 9/2016 | Trieu | |
| 2017/0014235 | A1 | 1/2017 | Jones et al. | |
| 2017/0020685 | A1 | 1/2017 | Geisler | |
| 2017/0042698 | A1 | 2/2017 | Saidha et al. | |
| 2017/0095337 | A1 | 4/2017 | Pasini et al. | |
| 2017/0119538 | A1 | 5/2017 | Baynham | |
| 2017/0312096 | A1 | 11/2017 | Liu | |
| 2017/0325966 | A1 | 11/2017 | Capote | |
| 2017/0348114 | A1 | 12/2017 | Jones et al. | |
| 2017/0367845 | A1 | 12/2017 | Eisen et al. | |
| 2018/0092752 | A1 | 4/2018 | Williams | |
| 2018/0116816 | A1* | 5/2018 | Weiman .................. | A61F 2/447 |
| 2018/0140427 | A1 | 5/2018 | Conway et al. | |
| 2018/0221156 | A1 | 8/2018 | Jones et al. | |
| 2018/0228570 | A1 | 8/2018 | Jones et al. | |
| 2018/0228612 | A1 | 8/2018 | Jones et al. | |
| 2018/0228613 | A1 | 8/2018 | Jones et al. | |
| 2018/0243094 | A1 | 8/2018 | Jones et al. | |
| 2018/0243097 | A1 | 8/2018 | Jones et al. | |
| 2018/0280139 | A1 | 10/2018 | Jones et al. | |
| 2018/0280140 | A1 | 10/2018 | Jones et al. | |
| 2018/0280141 | A1 | 10/2018 | Jones et al. | |
| 2018/0280144 | A1 | 10/2018 | Jones et al. | |
| 2018/0280145 | A1 | 10/2018 | Jones et al. | |
| 2018/0296350 | A1 | 10/2018 | Hamzey | |
| 2018/0318099 | A1 | 11/2018 | Altarac | |
| 2018/0318100 | A1 | 11/2018 | Altarac | |
| 2018/0368990 | A1 | 12/2018 | Saidha et al. | |
| 2018/0368992 | A1 | 12/2018 | Zink | |
| 2019/0133778 | A1 | 5/2019 | Johnston | |
| 2019/0133783 | A1 | 5/2019 | Unger et al. | |
| 2019/0150910 | A1 | 5/2019 | Jones et al. | |
| 2019/0209215 | A1 | 7/2019 | Baynham | |
| 2019/0250438 | A1 | 8/2019 | Oton | |
| 2019/0290441 | A1 | 9/2019 | Tong | |
| 2019/0343638 | A1 | 11/2019 | Jones et al. | |
| 2019/0343644 | A1 | 11/2019 | Ryan | |
| 2020/0000595 | A1 | 1/2020 | Jones et al. | |
| 2020/0038069 | A1 | 2/2020 | Jones | |
| 2020/0138595 | A1 | 5/2020 | Shoshtaev | |
| 2020/0155326 | A1 | 5/2020 | Hunt | |
| 2020/0261243 | A1 | 8/2020 | Unger et al. | |
| 2020/0281736 | A1 | 9/2020 | Milz | |
| 2020/0337856 | A1 | 10/2020 | Moore et al. | |
| 2020/0375726 | A1 | 12/2020 | Limem et al. | |
| 2021/0330473 | A1 | 10/2021 | Hunt | |
| 2022/0015925 | A1 | 1/2022 | Joly | |
| 2022/0117753 | A1* | 4/2022 | Rucker ................. | A61F 2/4455 |
| 2022/0168108 | A1 | 6/2022 | Laine | |
| 2023/0022520 | A1 | 1/2023 | Laine et al. | |

FOREIGN PATENT DOCUMENTS

| | | |
|---|---|---|
| EP | 1506753 | 2/2005 |
| EP | 2647453 | 10/2013 |
| EP | 1887954 | 9/2014 |
| EP | 2992846 | 3/2016 |
| KR | 200188509 Y | 7/2000 |
| KR | 101398889 | 5/2014 |
| KR | 101 830 547 | 4/2018 |
| WO | WO-1999033641 | 7/1999 |
| WO | WO-0217823 | 3/2002 |
| WO | WO-2009091627 | 7/2009 |
| WO | WO-2011022550 | 2/2011 |
| WO | WO-2014052477 | 4/2014 |
| WO | WO-2014160389 | 10/2014 |
| WO | WO-2014172495 | 10/2014 |
| WO | WO-2015053890 | 4/2015 |
| WO | WO-2015164982 | 11/2015 |
| WO | WO-2016023403 | 2/2016 |
| WO | WO-2016061148 | 4/2016 |
| WO | WO-2016130878 | 8/2016 |
| WO | WO-2017214114 | 12/2017 |
| WO | WO-2018152077 | 8/2018 |
| WO | WO-2018156905 | 8/2018 |
| WO | WO-2018182834 | 10/2018 |
| WO | WO-2018183809 | 10/2018 |
| WO | WO-2020023938 | 1/2020 |

OTHER PUBLICATIONS

Babaee S., et al., "Mechanical properties of open-cell rhombic dodecahedron cellular structures," Acta Materialia, vol. 60:2873-2885 (2012).

Chandran R.; "Optimization of Support Structures in Additive Manufacturing Process", Dissertation, University of Miami, 2016 (Year:2016).

European Search Report, 17810838.7, dated Dec. 19, 2019, 8 pages.

Hoffmann, W. et al., "Rapid prototyped porous nickel-titanium scaffolds as bone substitutes," Journal of Tissue Engineering, vol. 5:1-14 (2014).

International Preliminary Report on Patentability, PCT/US2017/36111, dated Jun. 27, 2018, 26 pages.

International Search Report and Written Opinion, PCT/US2017/36111, dated Nov. 6, 2017, 10 pages.

International Search Report and Written Opinion, PCT/US2018/017919, dated Jun. 6, 2018, 14 pages.

International Preliminary Report on Patentability, PCT/US2018/017919, dated Aug. 20, 2019, 11 pages.

International Preliminary Report on Patentability, PCT/US2018/019437, dated Aug. 27, 2019, 16 pages.

International Search Report and Written Opinion, PCT/US2018/019437, dated Jun. 28, 2018, 19 pages.

International Search Report and Written Opinion, PCT/US2018/014720, dated Jun. 1, 2018, 13 pages.

International Search Report and Written Opinion, PCT/US2018/025351, dated Jun. 8, 2018, 14 pages.

International Search Report and Written Opinion, PCT/US2019/043803, dated Nov. 7, 2019, 11 pages.

Leary M., et al.; "Optimal topology for additive manufacture: A method for enabling additive manufacture of support-free optimal structures", Materials and Design, 2014, vol. 63, p. 678-690 (Year: 2014).

Nouri, A., "Titanium foam scaffolds for dental applications," Metallic Foam Bone, Chapter 5: 130-160 (2017) http://dx.doi.org/10.1016/B978-0-08-101289-5.00005-6.

Strano G., et al.; "A new approach to the design and optimization of support structures in additive manufacturing", Int. J. Adv Manufacturing Technology, 2013, 66, p. 1247-1254 (Year: 2013).

(56) References Cited

OTHER PUBLICATIONS

Stryker, "Tritanium PI Cage", Technical Data Sheet, https://www.stryker.com/builttofuse/; retrieved from wayback machine on Apr. 23, 2021; date Jun. 21, 2016.
Supplementary EP Search Report (EP 19 84 0280), (2 pgs) dated Apr. 14, 2022.
Zhang,X., et al., "Additively Manufactured Scaffolds for Bone Tissue Engineering and the Prediction of their Mechanical Behavior: A Review," Materials, 10(10): 1-28 (2017).

* cited by examiner

SENSOR ENABLED INTERBODY IMPLANTS AND METHODS FOR MANUFACTURING SAME

CROSS-REFERENCE TO RELATED APPLICATIONS

The present application claims the benefit of U.S. Patent Application No. 63/770,387, entitled "SENSOR ENABLED INTERBODY IMPLANTS AND METHODS FOR MANUFACTURING SAME" filed on Mar. 12, 2025, which is incorporated herein by reference in its entirety.

FIELD

The present disclosure relates to three-dimensional lattice structures used in interbody implants and methods for manufacturing such structures, and particularly to biocompatible sensor-enabled three-dimensional lattice structures and methods for manufacturing such structures.

BACKGROUND

Monitoring patient recovery after implantation of interbody structures is a crucial part of a treatment plan. Presently, monitoring patient recovery often involves receiving patient feedback and conducting follow-up imaging (e.g., X-ray or Magnetic Resonance Imaging ("MRI") to evaluate placement and performance of the implant and detect possible issues, such as dislocation or infection. However, these sources (i.e., imaging modalities and patient feedback) often provide limited and discrete data point about patient's recovery and progress and cannot provide continuous, real-time information on patient's recovery and progress.

Sensors have been utilized along with interbody implants to provide real-time information on implant performance and patient recovery. For example, temperature and pressure sensors have been used in femoral and tibial inserts to monitor knee joint implant performance. Sensors have also been used in bone fusion cages and inserts to measure factors pertinent to monitoring recovery, such as strain, pressure, load, and temperature. However, most such sensor systems are used in inserts and cages with high stiffness implant bodies that do not and cannot measure the loading strain imposed within the body of the implant. The sensors in such implants are typically positioned on or near the surface of a loadbearing structure to directly measure the load applied to the loadbearing surfaces. For example, such arrangements are disclosed in US Pre-grant Publication No. 2025/0161694, the teachings of which is incorporated by reference in its entirety.

BRIEF SUMMARY

The present disclosure relates to sensor-enabled, low-stiffness, interbody implants and methods for manufacturing such implants. In one aspect, an interbody implant is disclosed. The interbody implant comprises an upper endplate that has a first surface and a second surface that contacts a first segment of tissue upon implantation, a lower endplate that has a first surface and a second surface that contacts a second segment of tissue upon implantation, and an implant body that extends between the first surface of the upper endplate and the first surface of the lower endplate. The implant body has a three-dimensional lattice structure that has a lower elastic modulus than an elastic modulus of the upper and lower endplates, and the upper and lower endplates are configured such that upon implantation into the body, one of the upper and lower endplates is a loadbearing endplate. The implant body further comprises a cavity and a sensor that is within the cavity along a loading direction of the implant such that a load applied to the loadbearing endplate is transferred from the loadbearing endplate, via the implant body, to the sensor.

In another aspect, a method for manufacturing of an interbody implant is disclosed. The method involves manufacturing a first endplate having a first surface and a second surface configured to contact a first segment of tissue upon implantation, manufacturing a second endplate having a first surface and a second surface configured to contact a second segment of tissue upon implantation, manufacturing an implant body comprising a three-dimensional lattice structure having a lower elastic modulus than an elastic modulus of the first and second endplates, manufacturing a cavity within the implant body, coupling the implant body to the first and second endplates such that the first and second endplates are separated substantially only via the implant body, and loading a sensor within the cavity in a loading direction of the implant such that a load applied to the loadbearing endplate is transferred from the loadbearing endplate, via the implant body, to the sensor.

In other examples, the aspects above, or any interbody implant, device, system, method, apparatus described herein can include one or more of the following features.

The sensor can comprise at least one of a vibration sensor, a force sensor, a resonant force sensor, a piezoelectric sensor, a pressure sensor, a capacitance sensor, a temperature sensor, an optical sensor, a flow sensor, a displacement sensor, an accelerometer, and a strain gauge.

Further, the interbody implant can comprise a seal configured to seal the sensor within the cavity of the interbody implant. The seal can comprise an extension configured to couple the seal to an external surface of the interbody implant. In some implementations, the external surface of the interbody implant can comprise a receptacle configured to mate with the extension of the seal to seal the sensor within the cavity of the implant body. The seal can further comprise a housing configured to house electronic components of the sensor. Furthermore, the seal can comprise a tool engagement area configured to facilitate implantation of the intrabody implant.

The sensor can further comprise a transmitter configured to transmit sensor data to a remote entity. The sensor can be coupled to the remote entity via a communications network.

The interbody implant can further comprise two or more sensors, each positioned along the loading direction of the implant at different locations within the implant body. In some implementations, the implant body can comprise two or more cavities, each configured to house one of the two or more sensors.

Other aspects and advantages of the invention can become apparent from the following drawings and description, all of which illustrate the various aspects of the invention, by way of example only.

BRIEF DESCRIPTION OF THE DRAWINGS

A detailed description of various embodiments is provided herein below with reference, by way of example, to the following drawings. It will be understood that the drawings are examples only and that all reference to the drawings is made for the purpose of illustration only and is not intended to limit the scope of the embodiments described herein below in any way. For convenience, reference numerals may also be repeated (with or without an offset) throughout the figures to indicate analogous components or features.

DETAILED DESCRIPTION

Figure 1A:
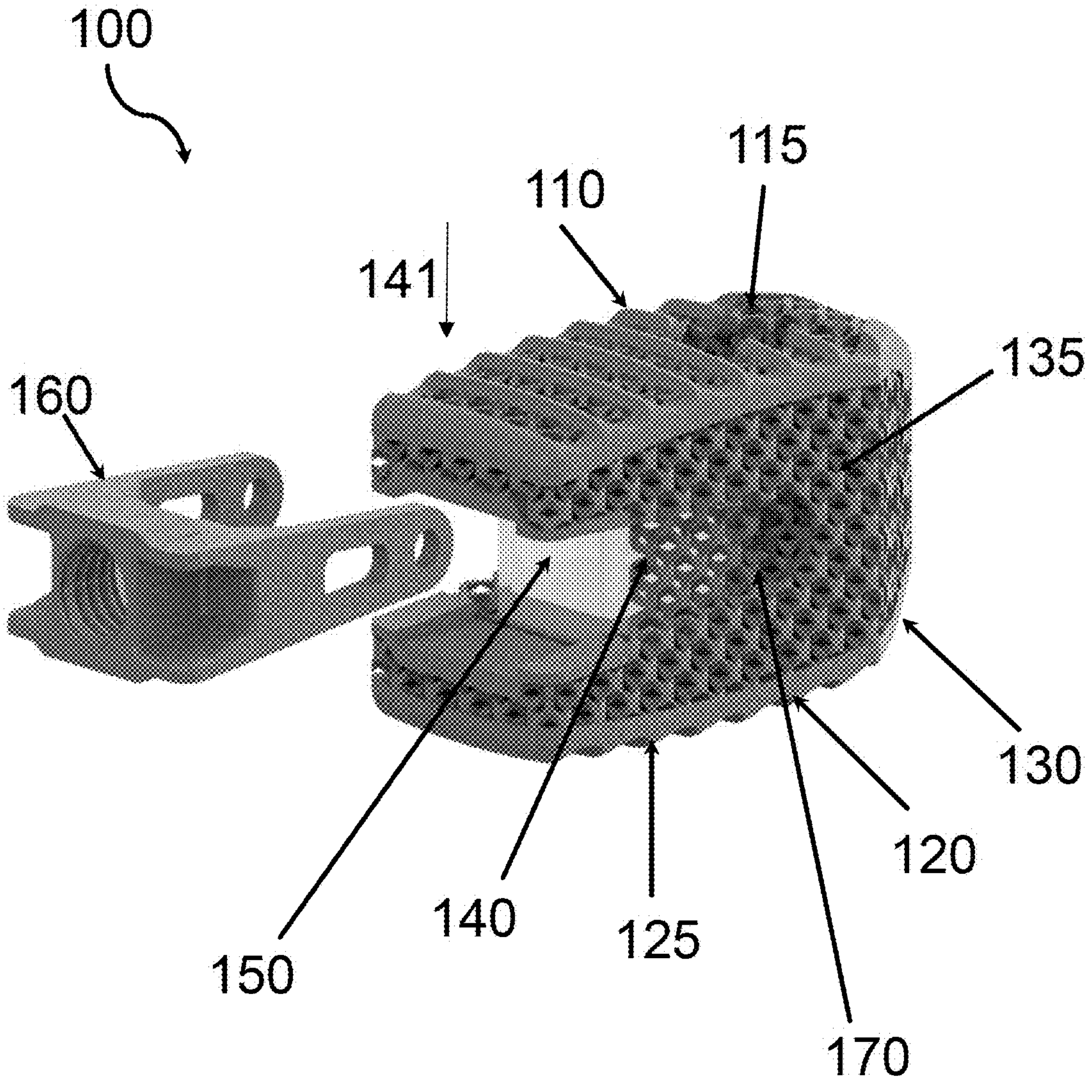
FIG. 1A is a schematic illustration of an isometric view of a sensor-enabled interbody implant with a seal detached from the implant according to embodiments disclosed herein.
Figure 1B:
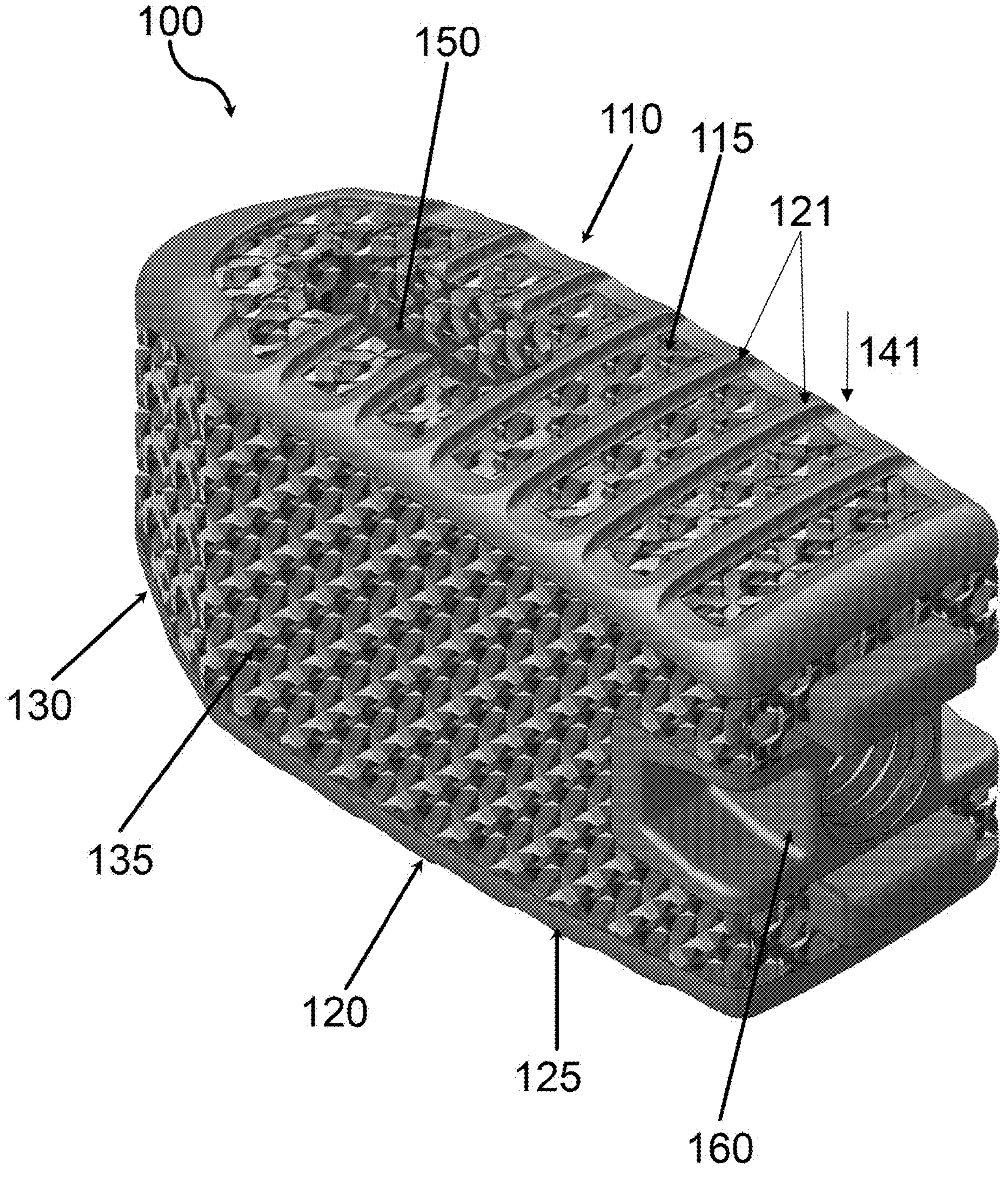
FIG. 1B is a schematic illustration of an isometric view of a sensor-enabled interbody implant with the seal coupled to the implant according to embodiments disclosed herein.
Figure 1C:
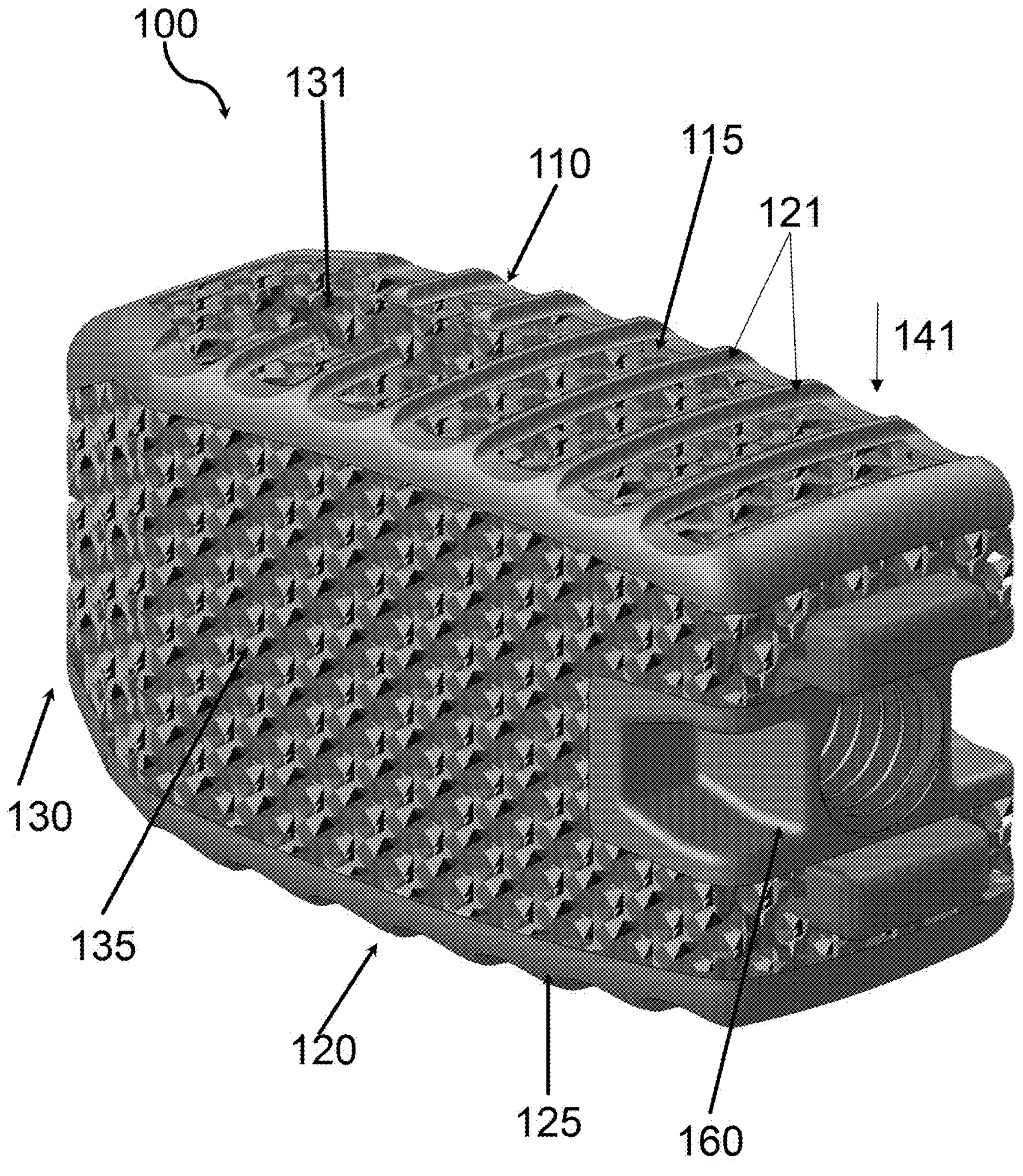
FIG. 1C is a schematic illustration of an isometric view of a sensor-enabled interbody implant with the seal coupled to the implant according to embodiments disclosed herein.
Figure 1D:
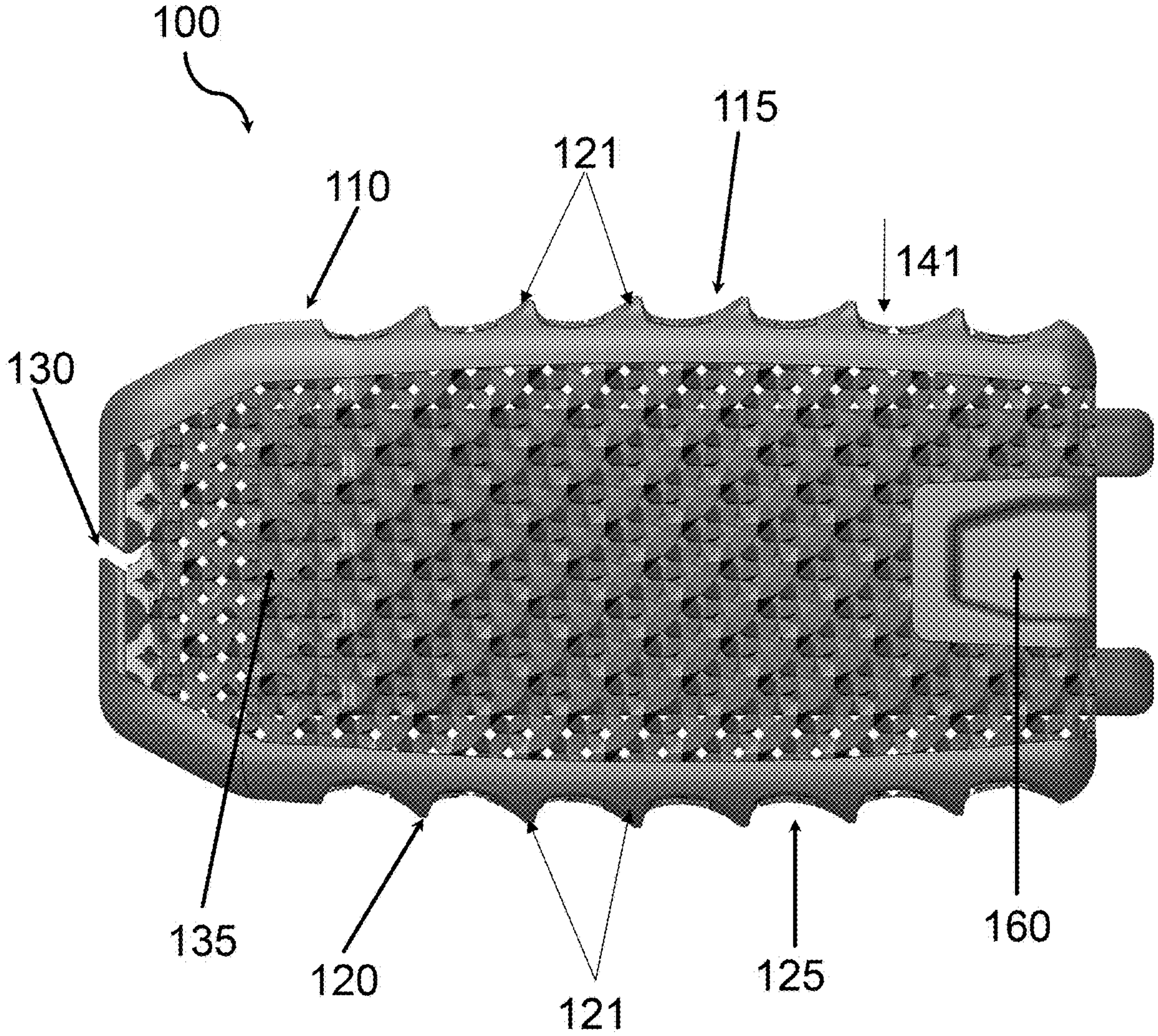
FIG. 1D is a schematic illustration of a side elevation view of a sensor-enabled interbody implant with the seal coupled to the implant according to embodiments disclosed herein.

The present disclosure relates to sensor-enabled three-dimensional interbody implants and methods for manufacturing such implants. The implants disclosed herein provide a three-dimensional, low stiffness, scaffold that promotes bone growth and osteointegration over time.

FIGS. 1A-1D depict schematic illustrations of isometric (FIGS. 1A-1C) and side elevation (FIG. 1D) views of a sensor-enabled implant 100 according to embodiments disclosed herein. The sensor-enabled implant 100 can be inserted between two bony surfaces creating a healing site between the two bony surfaces. The sensor is utilized to measure the load within the sensor-enabled implant 100. Referring to FIGS. 1A-1D, the sensor-enabled implant 100 comprises a body 130 that provides a mechanical spacing between the endplates of the adjacent vertebrae and mechanical stability to promote bone growth, allowing the vertebrae to fuse together over time.

The sensor-enabled implant 100 can be any interbody implant. For example, the implant can be an interbody implant that provides mechanical spacing between bony structures. In some implementations, the implant 100 can be a posterior lumbar interbody fusion (hereinafter "PLIF") implant or transforaminal lumbar interbody implant (hereinafter "TLIF").

Referring to FIGS. 1A-1D, the sensor-enabled implant 100 comprises an upper endplate 110, a lower endplate 120, and a body 130 that extends between the upper endplate 110 and the lower endplate 120. The upper endplate 110 and the lower endplate 120 are mechanically connected substantially only via the body 130. The upper and lower endplates 110,120 can comprise a biocompatible material and have a higher elastic modulus in the superior to inferior direction than the body 130. The endplates 110, 120 can configured such that upon insertion into the body, the upper surface 115 of the upper endplate 110 contacts a first segment of tissue (not shown) and the lower surface 125 of the lower endplate 120 contacts a second segment of tissue (not shown). The upper and lower endplates 110, 120 are further arranged such that upon implantation in the body, one of the endplates is a loadbearing endplate.

The body 130 can comprise a biocompatible material that has a lower elastic modulus than the elastic modulus in the superior to inferior direction of the upper 110 and lower 120 endplates. The body 130 further comprises a lattice structure 135. The lattice structure can comprising a plurality of repeating unit cells (described below) defined by a plurality of struts and nodes. For example, the lattice structure 135 can be a metallic lattice structure. Implants utilizing three-dimensional lattice structures are disclosed in U.S. application Ser. No. 17/967,503, U.S. Pat. No. 12,036,126, entitled "Three-Dimensional Lattice Structures for Implants" and U.S. application Ser. No. 17/964,814, U.S. Pat. No. 11,931,266, entitled "Implant with Independent Endplates," the teachings of which are incorporated by reference herein in their entirety.

The upper endplate 110 and lower endplate 120 can be independent of one another, such that they can move independently of one another. The term "independent," as used herein, refers to the ability of surfaces or volumes to move relative to another rather than refer to the lack of a mechanical connection. For instance, the upper endplate 110 and lower endplate 120 are disposed on opposite sides of a body 130 and can move independently of one another. The amount of independent movement can be determined largely by the elastic modulus of the body 130. The endplates 110, 120 can be connected substantially only via the body 130. Alternatively or additionally, the endplates 110, 120 can be connected substantially only via a connecting structure taking the function of the body 130.

As used herein, a connection "substantially via" an element refers to a structure where the element providing the connection provides at least 50% of a construct elastic modulus in a direction from one endplate to another. For example, the endplates 110, 120 can be connected substantially only via the body 130, where the body 130 provides at least 50% of a construct elastic modulus in a direction from one endplate to another. In some implementations, the endplates 110, 120 can be connected substantially only via the body 130, where the body 130 provides at least 75% of a construct elastic modulus in a direction from one endplate to another. Alternatively or additionally, the endplates 110, 120 can be connected substantially only via the body 130, where the body 130 provides at least 90% of a construct elastic modulus in a direction from one endplate to another.

The body 130 preferably provides mechanical spacing between the adjacent bony structures or vertebrae and provides adequate rigidity between the structures to allow for bone ingrowth. The use of a body 130 with a lower elastic modulus than the endplates 110 and 120 can allow the new bone growth to be stressed while ingrowth occurs, resulting in a stronger fused bone. The relatively higher stiffness of the endplates 110 and 120 distributes the load across the surface of the less stiff body 130 and reduces the occurrence of the bony structures or vertebral endplates from indenting the upper or lower surface of the body 130. As shown in FIGS. 1A-1D, the body 130 can further include at least one or more cavities 140, in which at least one sensor 150 is disposed. For example, each cavity 140 can be configured to include a sensor 150.

As shown in FIGS. 1A-1D, the endplates 110 and 120 can use optional raised ridges or teeth 121 to mechanically anchor the endplates 110 and 120 to bony structures or the endplates of the adjacent vertebrae. The ridges 121 extend from the endplates 110 and 120 to the surface of the body 130 that extends to the superior and inferior surface of the device. In addition to distributing the load across the body 130 and anchoring the interbody fusion sensor-enabled implant 100 relative to the adjacent bony structures or vertebrae, the endplates 110 and 120 can allow for bone attachment, providing stability between the interbody fusion device and the endplates of the adjacent vertebrae.

Referring to FIGS. 1A-1D, the upper and lower endplates 110 and 120 can be made of a biocompatible material, such as a biocompatible metal, that allows for bone attachment, either to the material directly or through the application of a bioactive surface treatment. For example, the upper and lower endplates 110 and 120 can be made from titanium or an alloy thereof, providing strength to the endplates, with an optional bioactive coating. In some implementations, the upper and lower endplates 110 and 120 can be made from commercially pure titanium, providing strength to the end-plates, with an optional bioactive coating.

In some implementations, he upper and lower endplates 110, 120 may be comprised of a lattice or scaffold structure to allow for bone ingrowth, while maintaining the ability of the endplates to sustain high point loads. If the upper and/or lower endplates 110, 120 are comprised of a lattice or scaffold structure, they may be defined by their volumetric density. In some implementations, the upper and lower endplates 110, 120 can comprise a material or lattice comprising titanium or any alloys thereof with a volumetric density between and including 60% and 100%, 80% and 100%, 70% and 90%, 60% and 90%, and 60% and 64%. Further, the endplates 110, 120 can comprise a material or lattice comprising titanium or any alloys thereof with a volumetric density of less than 60%.

The upper endplate 110 and lower endplate 120 can be comprised of the same material and possess the same volumetric density and lattice structure (if any). For example, the upper endplate 110 and lower endplate 120 can be comprised of different materials, volumetric density and/or lattice structure. It could be desirable for the upper endplate 110 and lower endplate 120 to have different physical properties, where the strength and composition of the adjacent bone is different near their respective endplate.

The body 130 is comprised of an implantable material that provides a scaffold for bone growth. For example, the body 130 can be comprised of titanium or any alloys thereof, with an optional bioactive coating. Alternatively or additionally, the body 130 can be made from commercially pure titanium, with an optional bioactive coating, as a structural lattice that provides mechanical separation between the endplates 110, 120. For example, the body 130 can be comprised of a repeating RDD structural scaffold comprised of titanium or any alloys thereof with a volumetric density between and including 5% to 50%. Alternatively or additionally, the body 130 can be comprised of a repeating RDD structural scaffold comprised of titanium or any alloys thereof with a volumetric density between and including 5% to 10%, 10% to 18%, 18% to 25%, 25% to 38%, 35% to 50%, or 32% to 38%. The volumetric density ranges disclosed can be adjusted within the scope of the inventive concept to suit a different material or different lattice structure.

Further, the body 130 can be comprised of a lattice comprised of titanium or any alloys thereof with an elastic modulus in the superior to inferior direction of between and including 8 to 12 GPa, 1 to 5 GPa, 2 to 4 GPa, or 3 to 9 GPa. Alternatively or additionally, the body 130 can be comprised of a lattice comprising titanium or any alloys thereof with an elastic modulus in the superior to inferior direction of between and including 10 MPa to 300 MPa. Further, the body 130 can be comprised of a lattice comprising titanium or any alloys thereof with an elastic modulus in the superior to inferior direction of between and including 300 MPa to 2 GPa, 300 MPa to 4 GPa, or 300 MPa to 12 GPa. Generally, the body 130 can be comprised of a lattice comprising titanium or any alloys thereof with an elastic modulus in the superior to inferior direction that is substantially similar to the bulk elastic modulus in the superior to inferior direction of the adjacent bone.

By adapting the lattice structure and volumetric density of the material, any implantable material can be appropriate for the body 130. Further, the body 130 can be treated with one or more bioactive coatings in one or more areas to promote certain reactions. For instance, the body 130 can be treated with a bioactive coating, such as an HA coating, to promote bone growth.

The volumetric density of the body 130 may also be varied to adjust the mechanical stability offered by the sensor-enabled implant 100 in a particular direction. In one example, the body 130 has a higher elastic modulus at the front and back of the sensor-enabled implant 100.

Figure 2:
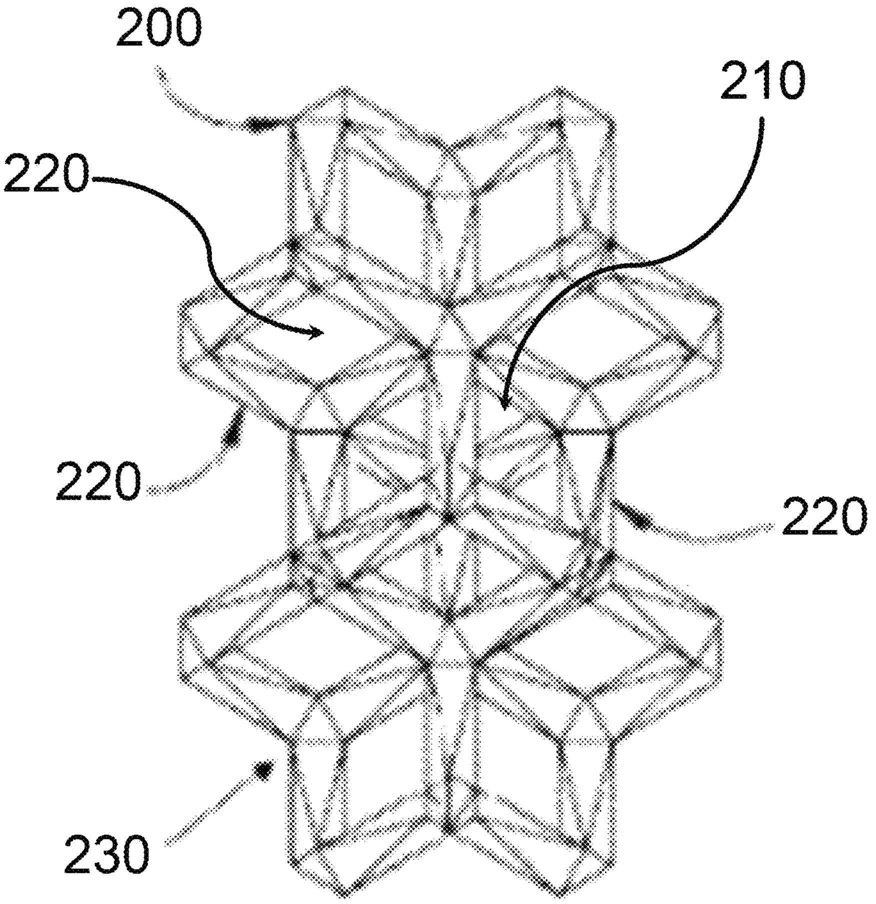
FIG. 2 is a high-level schematic illustration of a lattice structure according to embodiments disclosed herein.

FIG. 2 is a high-level schematic illustration of a front view of a lattice structure 200 according to embodiments disclosed herein. As shown, the lattice structure 200 can comprise a plurality of repeating unit cells 210. Each unit cell 210 is a three-dimensional shape comprising a plurality of sub-unit cells 220. Each sub-unit cell 220 is defined by a plurality of struts 220, each of which extends from a node 230 within the volume of the sub-unit cell 210, such that the struts 220 define the boundaries of the sub-unit cell 210.

As noted with reference FIGS. 1A-1D, the sensor-enabled implant 100 includes a cavity 140 configured to receive a sensor unit 150. The cavity 140 can extend along a loading direction 141 (i.e., a loading-bearing path) of the body 100. The sensor unit 150 is arranged in the cavity of the implant 100 such that it observes and records the load applied on the loadbearing endplate 110 (in this example, upper endplate 110), which is transferred to the body 130 and the cavity containing the sensor unit 150. As noted, the loadbearing endplate transfers and directs the force to the lattice body resulting in displacement of the body 130, this load is measured by the sensor 150. Transfer of the load to the sensor unit 150 is facilitated by the body 130, which is connected to the upper endplate 110 and surrounds the cavity 140 of the sensor unit 150. As noted, the body 130 has a lower elastic modulus than the elastic modulus of the endplates 110, 120, thereby allowing displacement and transfer of load via the body 130 to the sensor unit 150. The lattice-based configuration of the body along with the presence of the independent endplates allows the load on the loadbearing implant to transfer from the loadbearing end-plate through the body of the lattice to the sensor. Under this configuration, as the implant area heals and new bone/tissue develops, the amount of displacement in the lattice changes, resulting the load on the sensor to also undergo a change. This change in the load detected by the sensor is used to track healing and bone growth. These features of the sensor-enabled implant disclosed herein together provide a mechanism for tracking bone growth that has not been available in prior art implants.

The sensor unit 150 can comprise any suitable sensor known and available in the art. For example, the sensor unit 150 can comprise a vibration sensor, a force sensor, a resonant force sensor, a piezoelectric sensor, a pressure sensor, a capacitance sensor, a temperature sensor, an optical sensor, a flow sensor, a displacement sensor, an accelerometer, a strain gauge, or any other suitable sensor available in the art. Generally, any sensor capable of measuring load, displacement, or strain applied to the upper endplate 110 and transmitted via the body 130 to the sensor unit 150 can be utilized. The sensor unit 150 can further include any features or components known in the art that may be necessary for the operation of the sensor. In some implementations, an optical sensor can be utilized to measure the load applied to the implant as a function of detecting the light intensity within the cavity 140.

As noted, the sensor 150 can be any sensor capable of detecting load or displacement in the implant. In some implementations, the sensor can be configured to detect the load on one or more loadbearing areas of the implant. The sensor can be disposed in a location within the body of the implant that permits optimal measurements of the load on the upper and/or lower endplate and/or the load on the loadbearing areas and the implant body.

Figure 3:
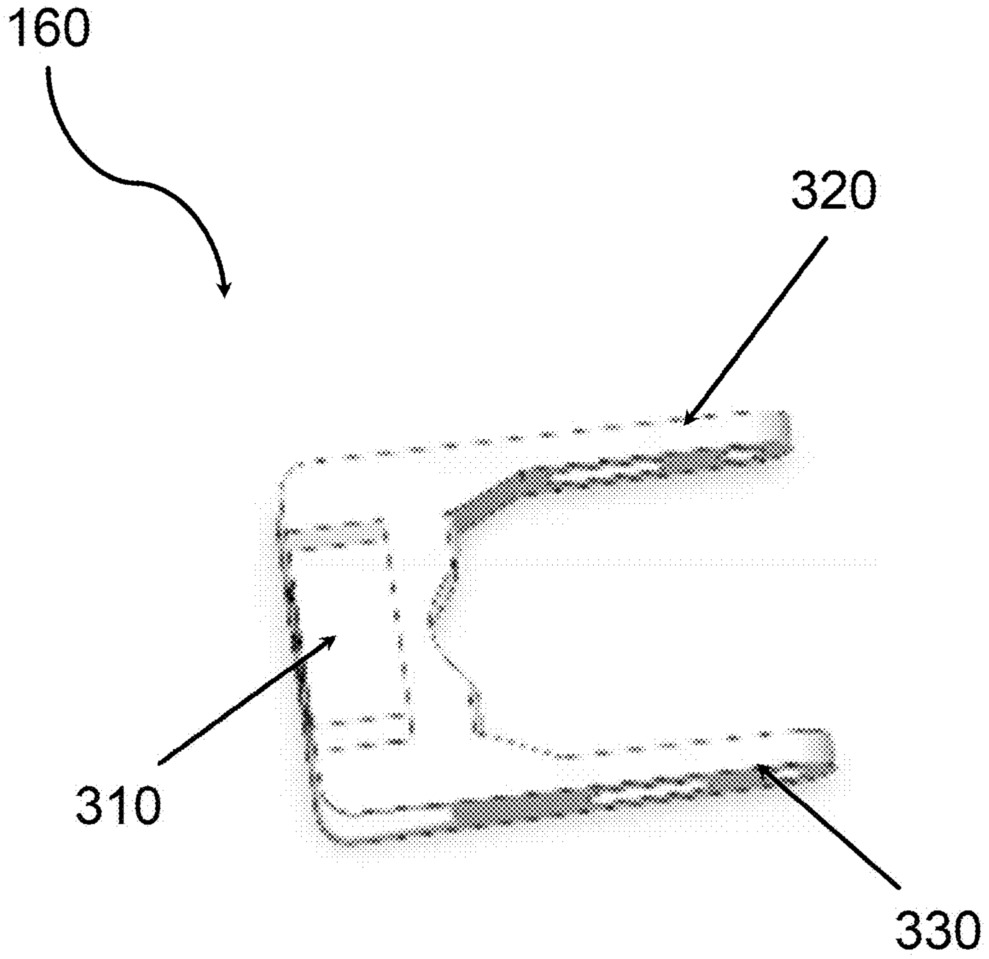
FIG. 3 is a schematic illustration of a sensor unit seal according to embodiments disclosed herein.
Figure 4:
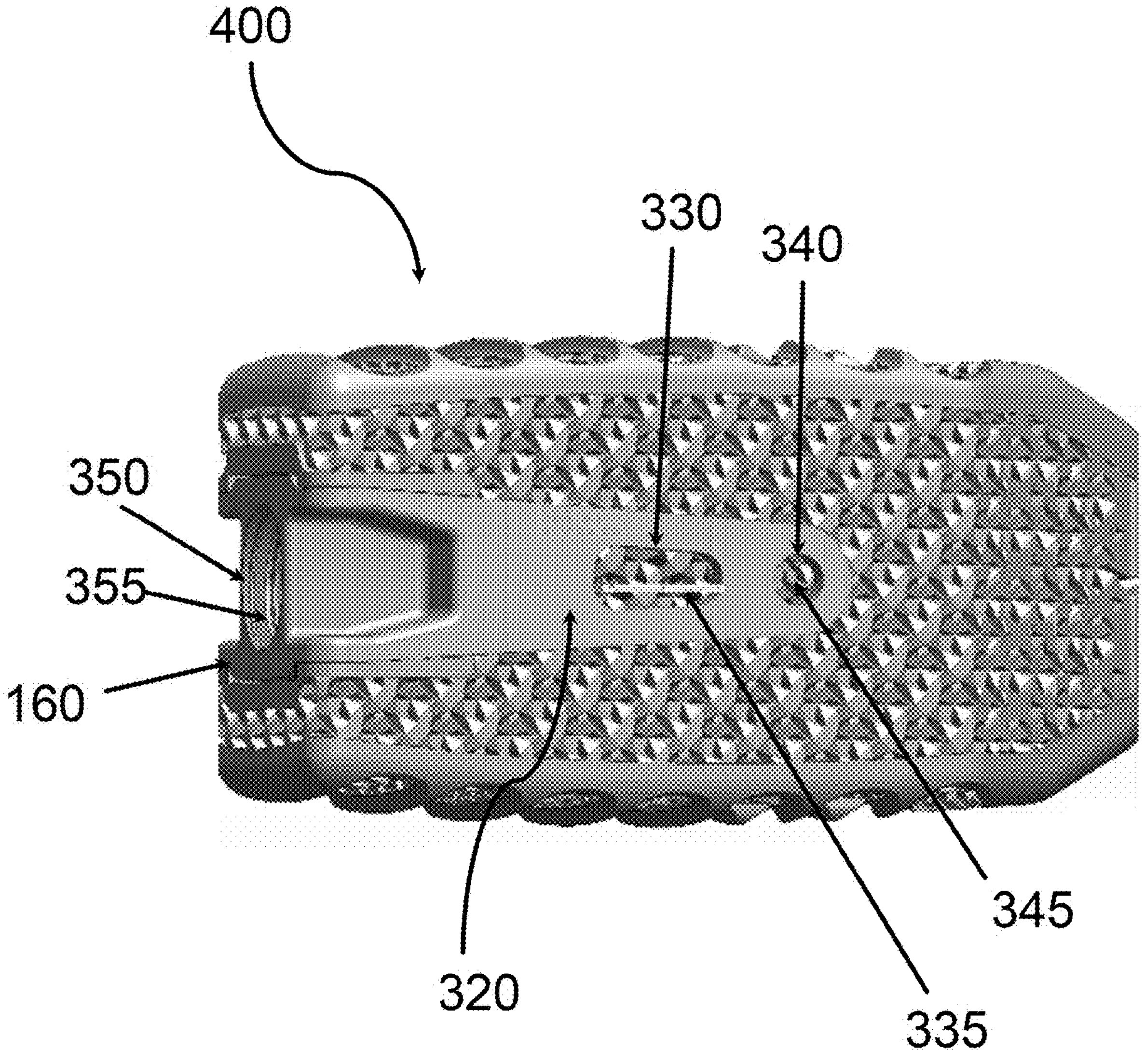
FIG. 4 is another schematic illustration of a sensor-enabled interbody implant according to embodiments disclosed herein.

Referring to FIGS. 1A-1D, the implant 100 further comprises a seal 160 that facilitates the placement of the sensor unit 150 into the cavity 140 and seals the sensor within the implant body 130. FIG. 3 is a schematic illustration of a sensor unit seal 160 according to embodiments disclosed herein. The seal 160 includes a housing 310 that houses the electronic components of the sensor unit 150. The seal also comprises one or more extensions 320, 330, each configured to mate with a corresponding receptacle 170 (FIG. 1B) in the implant body 130. As shown in FIG. 4, the extensions 320, 330 can include one or more mating features 330, 340 that are configured to mate with corresponding mating features 335, 345 of the receptacle(s) 170.

The housing 310 of the seal 160 can be configured to house the electronic components of the sensor, such as wires and battery that allow the sensor to function and generate data.

The seal 160 can further comprise a tool engagement area 350 configured to allow surgical tools to be fastened to the implant 400 during a surgical procedure. The tool engagement area 350 can comprise a threaded opening 355 that is configured to accept a threaded rod (not shown) to facilitate placement of the implant 400.

As shown in FIG. 4, which illustrates a sealed implant 400, the mating of the extension(s) 320 and 330 with the receptacle 170 seals the sensor unit within the cavity of the implant 400. Although placed along the loading direction, the receptacle 170 and the extensions 320, 330 can be configured such that they do not impede the loading of the implant 100.

In some implementations, the sensor unit 150 can comprise one or more features configured to promote bone-growth within the three-dimensional lattice of the implant body 130.

Figure 5:
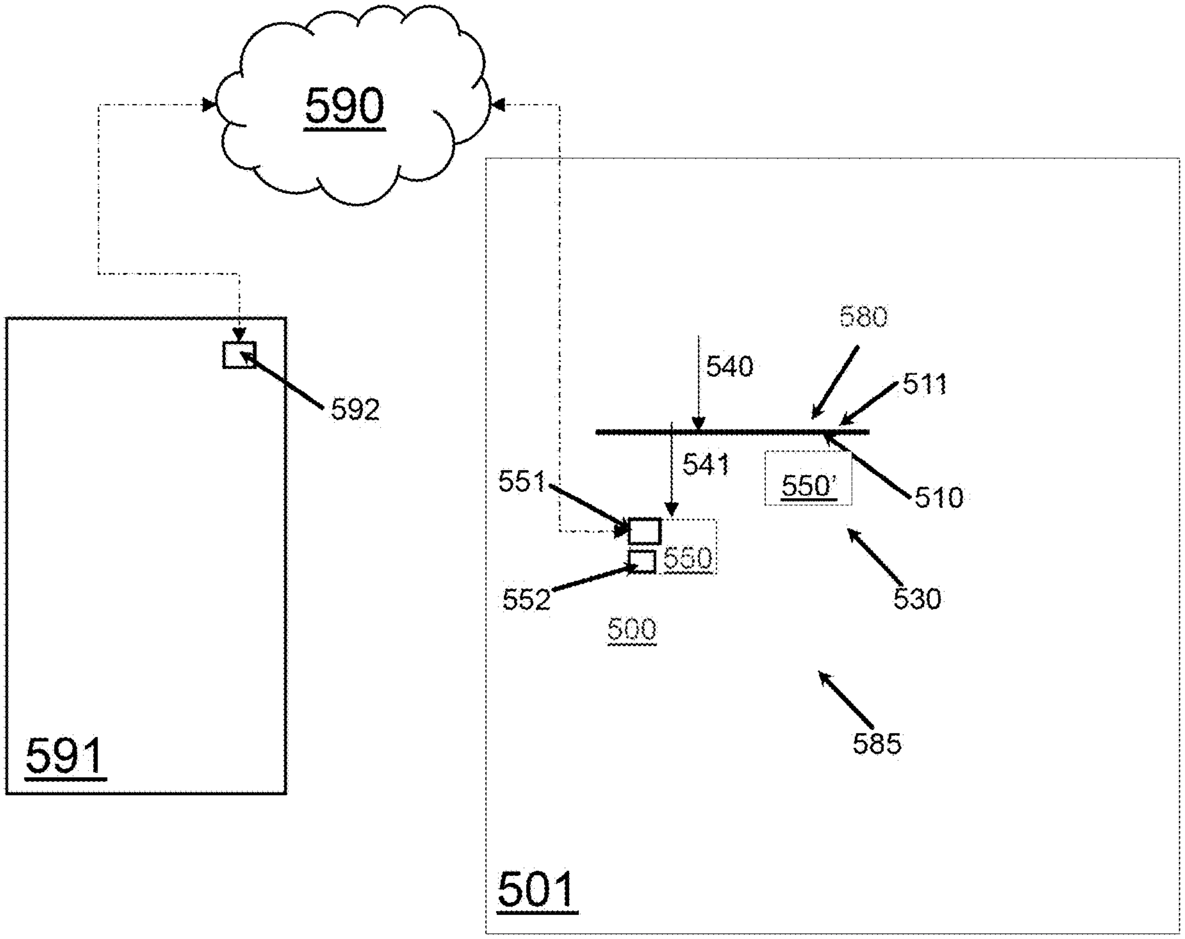
FIG. 5 is a high-level block diagram of a system for communicating with a sensor-enabled implant according to embodiments disclosed herein.

FIG. 5 is a high-level block diagram of a system for communicating with a sensor-enabled implant 500 according to embodiments disclosed herein. As shown in FIG. 5, a sensor-enabled implant 500 according to embodiments disclosed herein can be placed between two bony structures 580, 585 in a patient body 501 such that a first surface 511 of the upper endplate 510 of the implant 500 is adjacent to a surface of the first bony structure 580. The sensor unit 550 is positioned along the loading direction 540 such that the load applied to the upper endplate 510 is transferred (arrow 541) via the body to the sensor unit 550.

Referring to FIG. 5, the sensor unit 550 comprises a transmitter 551 configured to transmit data and information collected by the sensor unit 550 to another entity. For example, the transmitter 551 of the sensor unit 550 can be configured to communicate with a remote hand-held computer 510 (e.g., smart phone) or any other suitable device via a communications network 590. In some implementations, the transmitter 551 of the sensor unit 550 can be configured to communicate with the receiver 592 of a receiving device 591 (e.g., smart phone) via Bluetooth 590. Alternatively or additionally, the transmitter 551 of the sensor unit 550 can be configured to communicate with the receiver 592 of a receiving device 591 (e.g., smart phone or tablet) via Wi-Fi, NFC, Zigbee, infrared communication, ultra-wideband communication, radio-frequency signaling, or any other suitable wireless communication protocol. Generally, any suitable communications modality available in the art can be used with the embodiments disclosed herein. The receiving device can be any suitable device, for example a device having a computer software designed to track bone growth and healing in the implant.

In some implementations, the remote device can be a device that establishes a communications link with the sensor unit 550 upon coming into contact with a portion of the body 501 (e.g., when the receiving device 591 is placed on the skin over or in the vicinity of the implant 500).

A controller 552 (e.g., a microcontroller) can be coupled to the sensor unit 550 and configured to control the operations of the sensor unit 550. For example, the controller 552 can be configured to direct the transmitter 551 of the sensor to send data collected by the sensor and/or perform any suitable operation necessary to control the functions of the sensor unit 550. For example, the controller 552 can activate and/or disactivate the sensor unit 550. Generally, the sensor unit 550 can include any components known and available in the art that facilitate the operation of the sensor unit 550 and/or allow transmission, reception, collection, and storage of data collected by the sensor unit 550.

Additionally or alternatively, the controller 552 (and/or an additional controller—not shown) can be disposed outside of the sensor unit and/or outside of the body, for example in the remote device 510 and configured to control the operations of the sensor unit 550 and/or control transmission, reception, and/or collection of sensor data via the communications network 590.

The data collected from the sensor unit 550 can be collected and analyzed to determine status of bone fusion, bone growth, and healing. Further, the data can be used to provide a metric indicating rate of recovery, implant and/or surgery success, etc. The changes in the load experienced by the sensor unit 550 and transmitted by the transmitter 551 over time may indicate healing progression. For example, in some implementations, reduction of the load on the sensor unit 550 can indicate bone growth and healing.

Referring back to FIG. 1A, the sensor unit 150 can be disposed in any suitable place within the cavity of the implant 140 in the loading direction. Generally, the sensor unit 150 can be placed in any location that optimizes performance of the senor and collection of data. Further, in some implementations, the implant 100 can comprise two or more sensors, each disposed in a different location, along the loading direction, within the cavity of the implant 140. Generally, any number of sensors can be used in the loading direction within the implant cavity 140 to allow sensing of load in different regions of the implant body 130. For example, as shown in FIG. 5, two or more sensors 550, 550' can be used in different parts of the implant to assess bone growth, bone fusion, and/or healing in different regions of the implant 500. Generally, space permitting, sensors can be placed in any suitable location within the cavity.

The sensor unit 150 can comprise any suitable size that allows correct performance of the sensor and collection of data while maximizing the space in the implant body for allowing bone growth. For example, the sensor unit 150 can be configured such that it occupies no more than 5% to 30% of the overall volume of the implant body 130.

Those having ordinary skill in the art will appreciate that various changes can be made to the above embodiments without departing from the scope of the invention. Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

What is claimed is:

1. An interbody implant comprising:

an upper endplate having a first surface and a second surface, wherein the upper endplate is configured to contact a first segment of tissue upon implantation;

a lower endplate having a first surface and a second surface, wherein the lower endplate is configured to contact a second segment of tissue upon implantation;

an implant body extending between the first surface of the upper endplate and the first surface of the lower endplate, the implant body comprising a three-dimensional lattice structure having a lower elastic modulus than an elastic modulus of the upper and lower endplates, and the upper and lower endplates being configured such that upon implantation, one of the upper and lower endplates is a loadbearing endplate;

a cavity within the implant body; and a sensor disposed within the cavity along a loading direction of the implant such that a load applied to the loadbearing endplate is transferred from the loadbearing endplate, via the implant body, to the sensor.

2. The interbody implant of claim 1, wherein the sensor comprises at least one of a vibration sensor, a force sensor, a resonant force sensor, a piezoelectric sensor, a pressure sensor, a capacitance sensor, a temperature sensor, an optical sensor, a flow sensor, a displacement sensor, an accelerometer, and a strain gauge.

3. The interbody implant of claim 2, wherein the sensor is configured to detect the load applied to the loadbearing endplate.

4. The interbody implant of claim 3, further comprising a seal configured to seal the sensor within the cavity of the interbody implant.

5. The interbody implant of claim 4, further comprising an external surface, wherein the seal comprises an extension configured to couple the seal to the external surface of the interbody implant.

6. The interbody implant of claim 5, wherein the external surface of the interbody implant comprises a receptacle configured to mate with the extension of the seal to seal the sensor within the cavity of the implant body.

7. The interbody implant of claim 6, wherein the seal comprises a housing configured to house electronic components of the sensor.

8. The interbody implant of claim 7, wherein the seal comprises a tool engagement area configured to facilitate implantation of the interbody implant.

9. The interbody implant of claim 7, wherein the sensor comprises a transmitter configured to transmit sensor data to a remote entity.

10. The interbody implant of claim 7, wherein the sensor is configured to be coupled to a remote entity via a communications network.

11. The interbody implant of claim 7, further comprising two or more sensors, each positioned along the loading direction of the implant at different locations within the implant body.

12. The interbody implant of claim 11, wherein the implant body comprises two or more cavities, each configured to house one of the two or more sensors.

13. A method for manufacturing a sensor-enabled interbody implant, the method comprising:

manufacturing a first endplate having a first surface and a second surface, wherein the first endplate is configured to contact a first segment of tissue upon implantation;

manufacturing a second endplate having a first surface and a second surface, wherein the second endplate is configured to contact a second segment of tissue upon implantation;

manufacturing an implant body comprising a three-dimensional lattice structure having a lower elastic modulus than an elastic modulus of the first and second endplates;

manufacturing a cavity within the implant body;

coupling the implant body to the first and second endplates such that the first and second endplates are separated substantially only via the implant body;

loading a sensor within the cavity in a loading direction of the implant such that a load applied to the loadbearing endplate is transferred from the loadbearing endplate, via the implant body, to the sensor.

* * * * *